United States Patent

Mizutani et al.

[11] 3,968,124
[45] July 6, 1976

[54] PROCESS FOR PREPARING PHENYL-ACETIC ACID ESTERS

[75] Inventors: Toshio Mizutani; Nobuo Ohno; Yoshitaka Ume, all of Toyonaka; Takashi Matsuo, Nishinomiya, all of Japan

[73] Assignee: Sumitomo Chemical Company, Limited, Osaka, Japan

[22] Filed: Aug. 6, 1974

[21] Appl. No.: 495,155

[30] Foreign Application Priority Data
Aug. 28, 1973 Japan.............................. 48-97063

[52] U.S. Cl.......................... 260/340.5; 260/297 R; 260/567.6 M; 260/473 R; 260/476 R
[51] Int. Cl.²................ C07C 67/00; C07D 317/68; C07C 67/18
[58] Field of Search.......... 260/340.5, 473 R, 476 R

[56] References Cited
OTHER PUBLICATIONS
Wagner et al., Synthetic Organic Chemistry, John Wiley & Sons, Inc. (London) 1953, p. 484.
Smith, Open–Chain Nitrogen Compounds, W. A. Benjamin, Inc. (New York) 1965 pp. 23–25.

*Primary Examiner*—Richard L. Raymond
*Attorney, Agent, or Firm*—Sughrue, Rothwell, Mion, Zinn & Macpeak

[57] ABSTRACT

A process for preparing a substituted phenyl-acetic acid ester of the formula (I),

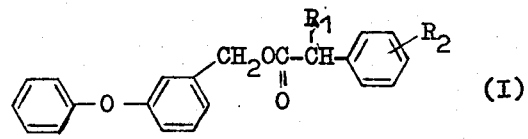

wherein $R_1$ is an ethyl group or an isopropyl group, $R_2$ is a hydrogen atom, a $C_1$–$C_4$ alkyl group, a methoxy group, a halogen atom or a methylenedioxy group, which comprises reacting a quaternary ammonium salt of the formula (III),

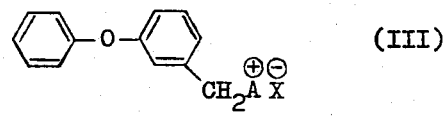

wherein X is a halogen atom, and A is an alkylamine, pyridine or an N-alkylaniline, with a carboxylic acid of the formula (II),

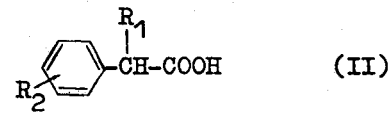

wherein $R_1$ and $R_2$ are each as defined above, its reactive derivative, or a mixture of the acid and its reactive derivative.

9 Claims, No Drawings

PROCESS FOR PREPARING PHENYL-ACETIC ACID ESTERS

BACKGROUND OF THE INVENTION

The present invention relates to a new process for preparing substituted phenyl-acetic acid esters comprising preparing quaternary ammonium salts from organo-halide compounds and amines, and then preparing the esters from the resulting quaternary ammonium salts.

SUMMARY OF THE INVENTION

An object of the present invention is to provide an industrially advantageous process for producing the excellent, low-toxic insecticides of the formula (I).

The present invention provides a process for preparing substituted phenyl-acetic acid esters of the formula (I),

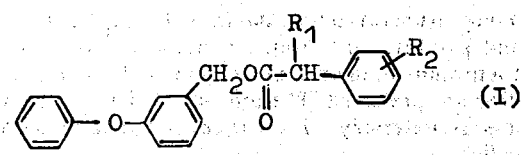

wherein $R_1$ is an ethyl group or an iso-propyl group, and $R_2$ is a hydrogen atom, a ($C_1$–$C_4$) alkyl group, a methoxy group, a halogen atom or a methylenedioxy group, comprising reacting a quaternary ammonium salt of the general formula (III),

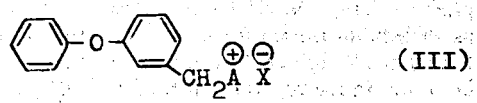

where X is a halogen atom and A is an alkylamine, pyridine or an N-alkylaniline with a substituted phenyl-acetic acid of the formula (II),

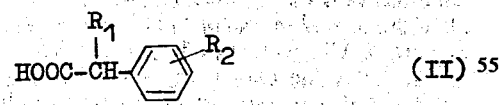

wherein $R_1$ and $R_2$ are each as defined above; with a mixture of the substituted phenyl-acetic acid and a reactive derivative thereof, e.g., the alkali metal salt, the ammonium salt or the alkylammonium salt of the substituted phenyl-acetic acid; or with a reactive derivative thereof, e.g., the alkali metal salt, the ammonium salt or the alkylammonium salt of the substituted phenyl-acetic acid.

An embodiment includes preparing the quaternary ammonium salt of the general formula (III), e.g., a 3-phenoxybenzyl alkylammonium halide, a 3-phenoxybenzyl pyridinium halide or a 3-phenoxybenzyl alkylarylammonium halide, as a useful intermediate of insecticides by reacting a 3-phenoxybenzyl halide of the general formula (IV),

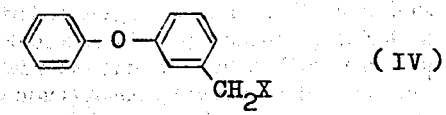

wherein X is a halogen atom with an alkylamine, pyridine or an N-alkylaniline.

DETAILED DESCRIPTION OF THE INVENTION

The ester compounds of the formula (I) have various advantages such as immediate onset of action, permeability, transfer into living plants, persistent pesticidal activity, metamorphosis disturbance, sterilization, and prohibition of egg-laying. Also, with respect to the spectrum of pesticidal activity, the compounds of the formula (I) exhibit a selective or non-selective activity on orders such as Coreoptera, Lepidoptera, Diptera, Orthoptera, Hemiptera, Homoptera and Acarus, and further are expected to be useful for controlling noxious insects such as a nematoda. Other important features of the compounds of the formula (I) are that they are active against noxious insects which are resistant to pesticides presently used, because their basic structures differ from those of known pesticides to which the insects are resistant, and that they have overall low toxicity to mammals including man.

The above-described process of this invention can be schematically shown as follows.

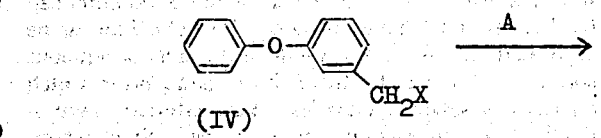

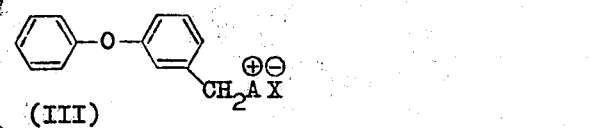

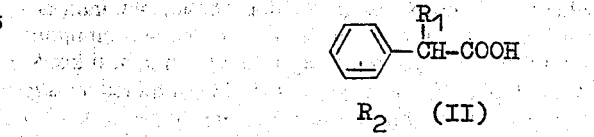

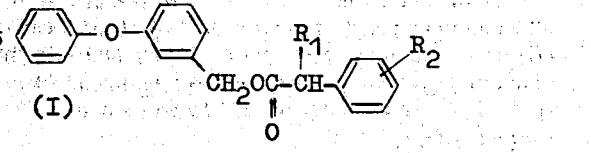

wherein X is a halogen atom, A is an alkylamine, pyridine or an N-alkylaniline, and $R_1$ and $R_2$ are each as defined above.

By studying an industrially advantageous preparation of the 3-phenoxybenzyl ester of the substituted phenylacetic acid of the formula (I), a method has been found in which the 3-phenoxybenzyl halide could be obtained in a high yield by halogenating the side chain of m-tolylphenylether. However, this reaction produces by-products such as 3-phenoxybenzalhalide and derivatives containing a nuclear halogen atom, in addition to the desired 3-phenoxybenzyl halide, and the resulting products are obtained as a mixture together with the starting materials. The direct isolation of the 3-phenoxybenzyl halide from the mixture obtained by fractional distillation is very difficult due to the low thermal stability of the desired 3-phenoxybenzyl halide and the by-products as well as staining and corrosion of the apparatus. In general, therefore, the isolation by fractional distillation is carried out after the components of the mixture are converted to more chemically stable derivatives, such as after acetylation. However, 3-phenoxybenzyl acetate has such a high boiling point (147° – 150°C/1mmHg) that the fractional distillation on an industrial scale is very limited instrumentally and thus becomes necessarily inefficient. Therefore, it has been desired to find an industrially advantageous separation from the mixture.

The method of separation of 3-phenoxybenzyl halide without this disadvantage and which is capable of mass production has been studied and a new process in which the compound can be separated from the reaction mixture, with ease and high purity, by converting it to a quaternary ammonium salt or the pyridinium salt has been found. That is, 3-phenoxybenzyl halide can be separated, in a form of crystals of the salts or aqueous solutions of the salts, from the organic layer which contains dissolved impurities. The quaternary ammonium salt and the pyridinium salt of the 3-phenoxybenzyl halide represented by the formula,

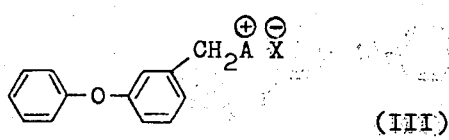

(III)

wherein A and X are as defined above, obtained according to the present invention are new compounds from which the desired final products, that is, the substituted phenyl-acetic acid, can be obtained easily, directly and in a high yield according to the following methods:

1. A method comprising reacting the quaternary ammonium salt or pyridinium salt of the formula (III) with the free acid of the formula (II), or with the alkali metal salt, the ammonium salt or the alkylammonium salt of the free acid of the formula (II) or with a mixture of the alkali metal salt, the ammonium salt or the alkylammonium salt of the free acid of the formula (II) and the free acid of the formula (II).

2. A method comprising converting the quaternary ammonium salt or the pyridinium salt of the formula (III) to the acetate by reaction with sodium acetate, hydrolyzing the resulting acetate to 3-phenoxybenzyl alcohol, and then reacting the alcohol with the acid chloride of the substituted phenyl-acetic acid of the formula (II).

3. A method comprising hydrolyzing the quaternary ammonium salt or the pyridinium salt of the formula (III) in dimethylformamide to 3-phenoxybenzyl alcohol, and then reacting the resulting alcohol with the acid chloride of the substituted phenyl-acetic acid of the formula (II).

As the halogen atom of the 3-phenoxybenzyl halides (IV) used according to the present invention, chlorine and bromine atoms are suitable. The benzyl halides can contain various halogen derivatives obtained, as by-products, by halogenation of m-tolylphenyl ether and unchanged m-tolylphenyl ether, based on the characteristics of the present invention. Examples of the other starting materials, that is, the alkylamine, the N-alkylaniline or pyridine, are exemplified by triethylamine, trimethylamine, diethylaniline, dimethylaniline, and pyridine, and from an industrial point of view, triethylamine, diethylaniline, dimethylaniline and pyridine are preferred. The amount of the tertiary amine used is preferably 1.1 to 2 times on a molar basis to the halide.

The quaternary salt can be formed by reacting the 3-phenoxybenzyl halide with an alkylamine, an N-alkylaniline or pyridine in inert solvents such as diethyl ether, benzene, toluene, xylene and chlorobenzene, at room temperature (e.g., about 20° – 30°C) or, if desired, up to the boiling point of the solvent. A preferred reaction temperature is 70° to 80°C.

The preparation of the ester compounds in the present invention will be illustrated in greater detail as follows.

The esters of the formula (I) can be obtained by reacting the quaternary ammonium salt or pyridinium salt of 3-phenoxybenzyl halide (III) with the substituted phenyl-acetic acid (II), in a suitable inert solvent such as dimethylformamide, acetone, methyl isobutyl ketone, anisole, toluene, xylene, chlorobenzene or nitrobenzene. In the reaction, heating is preferred to accelerate the reaction. A part of the substituted phenyl-acetic acid (II) can be added in the form of its alkali metal salt (for example, the sodium or potassium salt), ammonium salt or alkylammonium salt (for example, the triethyl ammonium salt), also with the free acid to accelerate the anion exchange reaction with quaternary salts of the 3-phenoxybenzyl halide. Conversion of all of the acid of the formula (II) to its salt is also satisfactory. All or a part of the acid can be converted to its salt in the esterification reaction in situ, if desired.

Examples of quaternary salts of the 3-phenoxybenzyl halide (III) which can be used in the present invention are exemplified as follows.

3-Phenoxybenzyl triethyl ammonium chloride
3-Phenoxybenzyl triethyl ammonium bromide
3-Phenoxybenzyl dimethylphenyl ammonium bromide
3-Phenoxybenzyl diethylphenyl ammonium bromide
3-Phenoxybenzyl pyridinium chloride
3-Phenoxybenzyl pyridinium bromide These salts can be obtained by reacting the reaction mixture obtained after halogenation of the m-tolylphenyl ether with an alkylamine, an alkylarylamine or pyridine in an inert solvent such as benzene or toluene, and then filtering the resulting salt crystals or separating the salt in a form of an aqueous solution from the organic layer, and followed by evaporation up to dryness if desired.

Suitable examples of the substituted phenyl-acetic acids of the formula (II) are exemplified as follows.

α-Ethyl-phenylacetic acid
α-iso-Propyl-phenylacetic acid
4-Methyl-α-ethyl-phenylacetic acid
4-Methyl-α-iso-propyl-phenylacetic acid
4-Methoxy-α-ethyl-phenylacetic acid
4-Methoxy-α-iso-propyl-phenylacetic acid
4-Chloro-α-ethyl-phenylacetic acid
4-Chloro-α-iso-propyl-phenylacetic acid
4-Bromo-α-iso-propyl phenylacetic acid
4-Fluoro-α-iso-propyl-phenylacetic acid
3,4-Methylenedioxy-α-iso-propyl-phenylacetic acid
4-tert-Butyl-α-iso-propyl-phenylacetic acid The process for preparing compounds within the scope of the present invention is illustrated in greater detail by reference to the following examples, which are only illustrative and are not intended to be interpreted as limiting the scope of the present invention.

EXAMPLE 1

After 6.4 g of 3-phenoxybenzyl triethyl ammonium chloride was mixed with 50 ml of dimethylformamide, 4.1 g of sodium α-ethyl-phenyl acetate was added thereto at room temperature (about 20° – 30°C). The mixture was heated under reflux for 5 hours while stirring and cooled. After adding 200 ml of water, the resulting solution was extracted with benzene, and the benzene layer was washed successively with aqueous dilute hydrochloric acid, a saturated aqueous sodium chloride solution, a saturated aqueous sodium bicarbonate solution and a saturated aqueous sodium chloride solution, and then dried over anhydrous magnesium sulfate. Removal of benzene under reduced pressure gave 5.95 g of 3-phenoxybenzyl α-ethyl-phenyl-acetate ($n_D^{25}$ 1.5713).

EXAMPLE 2

After 7.3 g of 3-phenoxybenzyl triethyl ammonium bromide was mixed with 50 ml of dimethylformamide, 4.4 g of sodium α-isopropyl-phenyl acetate was added thereto at room temperature and then the mixture was heated under reflux for 8 hours while stirring.

Thereafter, the reaction mixture was treated in the same manner as described in Example 1 to obtain 6.5 g of 3-phenoxybenzyl α-isopropyl-phenyl acetate ($n_D^{27}$ 1.5587).

EXAMPLE 3

After 5.5 g of 3-phenoxybenzyl triethyl ammonium bromide was mixed with 50 ml of methyl isobutyl ketone, 3.5 g of sodium 4-methyl-α-ethyl-phenyl acetate was added thereto and then the mixture was heated under reflux for 10 hours while stirring. Thereafter, the reaction mixture was cooled and poured into 100 ml of water. The organic layer was separated and treated in the same manner as described in Example 1 to obtain 4.4 g of 3-phenoxybenzyl 4-methyl-α-ethyl-phenyl-acetate ($n_D^{26}$ 1.5695).

EXAMPLE 4

After 4.8 g of 3-phenoxybenzyl triethyl ammonium chloride was mixed with 30 ml of dimethylformamide, 4.3 g of 4-bromo-α-isopropyl-phenyl acetic acid was added thereto. Then 2.3 g of triethylamine was added dropwise thereto and the mixture was stirred for 1 hour at room temperature and then heated under reflux for 8 hours while stirring and cooled. After adding 200 ml of water, to the resulting solution, the solution was extracted with benzene, and the benzene layer was treated in the same manner as described in Example 1 to obtain 5.8 g of 3'-phenoxybenzyl 4-bromo-α-isopropyl-phenyl-acetate ($n_D^{25}$ 1.5790).

EXAMPLE 5

6.7 g of 3-phenoxybenzyl triethyl ammonium bromide, 5.8 g of sodium 4-bromo-α-ethylphenyl-acetate and 70 ml of xylene were treated in the same manner as described in Example 3 to obtain 7.3 g of 3'-phenoxybenzyl 4-bromo-α-ethyl-phenyl-acetate ($n_D^{24}$ 1.5842).

EXAMPLE 6

4.5 g of 3-phenoxybenzyl pyridinium chloride, 1.4 g of α-ethylphenyl-acetate and 50 ml of dimethylformamide were treated in the same manner as described in Example 1 to obtain 4.65 g of 3-phenoxybenzyl α-ethylphenyl-acetate ($n_D^{25}$ 1.5715).

EXAMPLES 7 TO 13

A mixture of 0.02 mole of 3-phenoxybenzyl triethyl ammonium bromide, 0.22 mole of the sodium salt of the substituted phenyl-acetic acid as shown in Table 1, and 70 ml of dimethylformamide was heated under reflux for 8 hours while stirring, and then treated in the same manner as described in Example 1. The results obtained are as shown in Table 1.

Table 1

| Example No. | Sodium Salt of Substituted Phenyl Acetic Acid Used | Substituted Phenyl Acetic Acid Ester Obtained Name | Yield (%) | Reactive Index ($n_D^{25}$) |
|---|---|---|---|---|
| 7 | Sodium 4-methyl-α-iso-propyl-phenyl-acetate | 3'-Phenoxybenzyl 4-methyl-α-isopropyl-phenyl-acetate | 85 | 1.5602 |
| 8 | Sodium 4-methoxy-α-iso-propyl-phenyl-acetate | 3'-Phenoxybenzyl 4-methoxy-α-isopropyl-phenyl-acetate | 90 | 1.5615 |
| 9 | Sodium 4-chloro-α-ethyl-phenyl-acetate | 3'-Phenoxybenzyl 4-chloro-α-ethyl-phenyl-acetate | 92 | 1.5720 |
| 10 | Sodium 4-chloro-α-iso-propyl-phenyl-acetate | 3'-Phenoxybenzyl 4-chloro-α-isopropyl-phenyl-acetate | 87 | 1.5645 |
| 11 | Sodium 4-fluoro-α-iso-propyl-phenyl-acetate | 3'-Phenoxybenzyl 4-fluoro-α-isopropyl-phenyl-acetate | 90 | 1.5538 |
| 12 | Sodium 3,4-methylenedioxy-α-isopropyl-phenyl-acetate | 3'-Phenoxybenzyl 3,4-methylenedioxy-α-isopropyl-phenyl-acetate | 86 | 1.5721 |
| 13 | Sodium 4-tert.butyl-α- | 3'-Phenoxybenzyl 4-tert.butyl- | 87 | 1.5149 |

Table 1-continued

| Example No. | Sodium Salt of Substituted Phenyl Acetic Acid Used | Substituted Phenyl Acetic Acid Ester Obtained | | |
|---|---|---|---|---|
| | | Name | Yield (%) | Reactive Index ($n_D^{25}$) |
| | isopropyl-phenyl-acetate | α-isopropyl-phenyl-acetate | | |

While the invention has been described in detail and with reference to specific embodiments thereof, it will be apparent to one skilled in the art that various changes and modifications can be made therein without departing from the spirit and scope thereof.

What is claimed is:

1. A process for preparing a substituted phenyl-acetic acid ester of the formula (I),

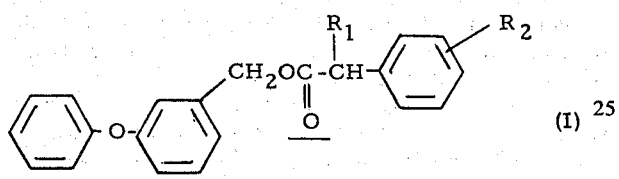

wherein $R_1$ is an ethyl group or an isopropyl group, $R_2$ is a hydrogen atom, a $C_1$–$C_4$ alkyl group, a methoxy group, a halogen atom or a methylenedioxy group, which comprises reacting in the presence of a solvent a quaternary ammonium salt of the formula (III),

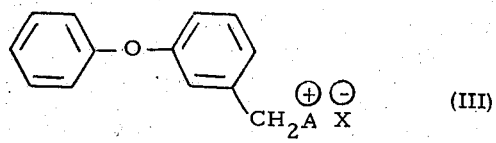

wherein X is a halogen atom, and $A^+$ is trialkylammonium, pyridinium or a dialkylanilinium group, with a carboxylic acid of the formula (II),

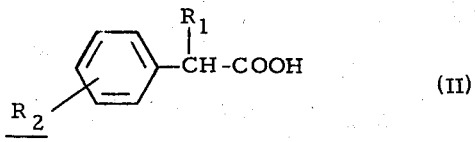

wherein $R_1$ and $R_2$ are each as defined above, its reactive derivative, or mixture of the acid and its reactive derivative, said reactive derivative of said carboxylic acid being a member selected from the group consisting of the alkali metal salt, the ammonium salt and the alkyl ammonium salt.

2. The process according to claim 1, wherein the reacting is under heating and in the presence of a solvent selected from the group consisting of dimethylformamide, acetone, methyl isobutyl ketone, anisole, toluene, xylene, chlorobenzene and nitrobenzene.

3. The process according to claim 1, including preparing the quaternary ammonium salt (III) by reacting a 3-phenoxybenzyl halide of the formula (IV),

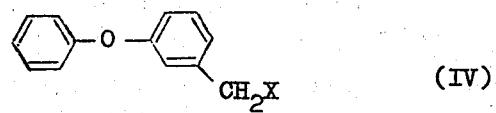

wherein X is a halogen atom with an amine selected from the group consisting of a tertiary alkylamine, pyridine and a tertiary N-alkylaniline.

4. The process according to claim 3, wherein the halogen atom is a chlorine atom or a bromine atom.

5. The process according to claim 3, wherein the amine is a member selected from the group consisting of triethylamine, trimethylamine, diethylaniline, dimethylaniline and pyridine.

6. The process according to claim 3, wherein the molar ratio of the amine to the 3-phenoxybenzyl halide of the formula (IV) is 1.1:1 to 2:1.

7. The process according to claim 3, wherein said reacting is in the presence of a solvent selected from the group consisting of diethyl ether, benzene, toluene, xylene and chlorobenzene.

8. The process according to claim 7, wherein the reacting is between room temperature and the boiling point of the solvent employed.

9. The process according to claim 8, wherein the reacting is between 70° to 80°C.

* * * * *